United States Patent
Furlong et al.

(10) Patent No.: US 9,560,992 B2
(45) Date of Patent: Feb. 7, 2017

(54) METHODS AND SYSTEMS FOR OBSERVATION OF TYMPANIC FUNCTION

(71) Applicants: Cosme Furlong, Worcester, MA (US); Saumil N. Merchant, Acton, MA (US); John J. Rosowski, Arlington, MA (US)

(72) Inventors: Cosme Furlong, Worcester, MA (US); Saumil N. Merchant, Acton, MA (US); John J. Rosowski, Arlington, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 14/879,400

(22) Filed: Oct. 9, 2015

(65) Prior Publication Data

US 2016/0128611 A1    May 12, 2016

Related U.S. Application Data

(62) Division of application No. 12/521,876, filed as application No. PCT/US2008/056505 on Mar. 11, 2008, now Pat. No. 9,155,459.

(60) Provisional application No. 60/894,305, filed on Mar. 12, 2007.

(51) Int. Cl.
| | |
|---|---|
| A61B 6/00 | (2006.01) |
| A61B 5/12 | (2006.01) |
| A61B 5/00 | (2006.01) |
| A61B 1/227 | (2006.01) |
| A61B 1/32 | (2006.01) |
| A61B 1/04 | (2006.01) |
| A61B 1/00 | (2006.01) |
| A61B 7/00 | (2006.01) |
| A61B 1/06 | (2006.01) |

(52) U.S. Cl.
CPC ........... *A61B 5/126* (2013.01); *A61B 1/00006* (2013.01); *A61B 1/00009* (2013.01); *A61B 1/04* (2013.01); *A61B 1/0661* (2013.01); *A61B 1/227* (2013.01); *A61B 1/32* (2013.01); *A61B 5/0084* (2013.01); *A61B 7/00* (2013.01)

(58) Field of Classification Search
CPC ....... A61B 1/227; A61B 1/042; A61B 5/0048; A61B 5/0097
See application file for complete search history.

*Primary Examiner* — Joseph M Santos Rodriguez
(74) *Attorney, Agent, or Firm* — Burns & Levinson LLP; Orlando Lopez

(57) ABSTRACT

Methods and systems for endoscopic observation of tympanic function.

6 Claims, 4 Drawing Sheets

METHODS AND SYSTEMS FOR OBSERVATION OF TYMPANIC FUNCTION

CROSS-REFERENCE TO RELATED APPLICATIONS

This application is a divisional of co-pending U.S. application Ser. No. 12/521,876, entitled METHODS AND SYSTEMS FOR OBSERVATION OF TYMPANIC FUNCTION, which in turn is a U.S. national stage application under 35 U.S.C. 371 of international Application No. PCT/US08/56505 filed on Mar. 11, 2008, which in turn claims priority to and benefit of U.S. Provisional Patent Application No. 60/894,305 filed on Mar. 12, 2007, both of which are incorporated herein in their entirety for all purposes.

BACKGROUND

Middle-ear disease is the cause of conductive hearing losses that affect nearly every person in the world at some time in their life. Most of these cases are due to acute infectious processes that are amenable to antibiotic treatment and are quickly resolved. However, a sizable fraction of these cases are due to chronic middle-ear disease, which is best treated by middle-ear surgery, i.e., opening of the mastoid to remove disease (mastoidectomy) and reconstruction of all or part of the middle-ear sound-conductive apparatus (tympanoplasty). There are over 70,000 middle-ear surgeries performed each year in the US.

While middle-ear disease is common, the differential diagnosis of the multiple pathologies responsible for these hearing losses is problematic. Even diagnosis of the common middle-ear effusion depends on expert observation or the use of screening systems that generate significant high false positive rates. Differential diagnosis of the pathology responsible for conductive hearing loss with an intact eardrum (tympanic membrane) and fluid-free middle ear is a particularly difficult problem, even for a trained otologist. Furthermore, while the surgery to cure ears of chronic disease is highly successful, the hearing results of middle-ear reconstructive procedures are generally poor, except for certain minimally invasive procedures such as stapes replacement surgery (stapedectomy).

Otoscopy and pneumatic otoscopy work well for the diagnosis of middle-ear effusion in well-trained hands, but the average clinician is not always capable of accurately performing these tests. Simple otoscopy is of little value in the diagnosis of ossicular disorders; pneumatic otoscopy is useful in expert hands, but the assessment of eardrum mobility is subjective and such expertise is not easy transferred to inexperienced clinicians. In the hands of a practiced observer, pneumatic otoscopy can sometimes aid in the diagnosis of reconstructive failures.

Tympanometry (and its cousin reflectometry) is one of the standard screening methods for the presence of middle-ear effusion. As a screener, tympanometry is fairly sensitive for middle ear effusion, but of less than perfect selectivity (there is a sizable percentage of false positives). The utility of tympanometry in differential diagnosis of ossicular disorders or evaluation of middle-ear reconstruction is limited. Tympanometry also shows limited sensitivity and selectivity in cases of ossicular disorders or chronic middle-ear disease.

Laser-Doppler vibrometry (LDV) has been successfully used in the differential diagnosis of ossicular disorders and the evaluation of middle-ear reconstructive procedures. It presently requires two people (a clinician observer and a computer operator) to make these measurements.

Therefore, there is a need for systems and methods for the observation of middle ear behavior that provide easier use and accurate measurements.

BRIEF SUMMARY

In one embodiment, the system of these teachings, for examining behavior of a membrane in a passage, includes a microphone, a sound generating component, a light delivery component, a miniature optical component; the microphone, the sound generating component, and the light delivery component being disposed in a periphery of the optical component. The embodiment of the system also includes an illuminating light source operatively connected to the light delivery component, where the microphone, the sound generating component, the optical component and the light delivery component are disposed in a speculum, and the speculum is adapted to permit examination of a passage, the light delivery component being capable of delivering light into the passage, where the optical component is capable of receiving a reflected/scattered portion of light delivered into the passage. An imaging component is disposed to receive light from the miniature optical component. The system further includes a reference light source, a modulating component disposed to receive light from the reference light source and capable of modulating light received from the reference light source, another optical component disposed to receive light from the modulating component and from the imaging component, where the other optical component is capable of providing light received from the imaging component and from the modulating component, and an image detecting component disposed to receive light from the other optical component. The image detecting component is disposed to receive light from the reference light source after being modulated and the reflected/scattered portion of the light delivered into the passage and is capable of detecting an interferometric recording (holographic recording) of the reference light and the reflected scattered portion of the light delivered into the passage. The holographic recording can provide information as to deformation and shape of the membrane.

A number of other embodiments of the system of these teachings are disclosed. Also, embodiments of the method of these teachings are also disclosed.

For a better understanding of the present teachings, together with other and further needs thereof, reference is made to the accompanying drawings and detailed description and its scope will be pointed out in the appended claims.

DETAILED DESCRIPTION

In the following descriptions of these teachings, the terms "light" and "optical radiation" may be used interchangeably, and these terms refer to electromagnetic radiation over the entire spectrum of wavelengths such as, for example, ultraviolet, visible, and infrared.

Similarly, the term "sound" refers to acoustic radiation over the entire available spectrum of wavelengths of such radiation, while not being limited to only the portion of the spectrum that is detectable by hearing.

In one embodiment, the system of these teachings, for examining behavior of a membrane in a passage, includes a miniature microphone, a miniature sound generating component, a miniature light delivery component, a miniature optical component; the miniature microphone, the miniature sound generating component, and the miniature light delivery component being disposed in a periphery of the miniature optical component. The embodiment of the system also includes an illuminating light source operatively connected to the miniature light delivery component, where the miniature microphone, the miniature sound generating component, the miniature optical component and the miniature light delivery component are disposed in a speculum, and the speculum is adapted to permit examination of a passage; the miniature light delivery component being capable of delivering light into the passage, where the miniature optical component is capable of receiving a reflected/scattered portion of light delivered into the passage. An imaging component is disposed to receive light from the miniature optical component. The system further includes a reference light source, a modulating component disposed to receive light from the reference light source and capable of modulating light received from the reference light source, another optical component disposed to receive light from the modulating component and from the imaging component, where the beam separating component is capable of providing light received from the imaging component and from the modulating component, and an image detecting component disposed to receive light from the other optical component. The image detecting component is disposed to receive light from the reference light source after being modulated and the reflected/scattered portion of the light delivered into the passage and is capable of detecting an interferometric recording (holographic recording) of the reference light and the reflected/scattered portion of the light delivered into the passage. The holographic recording can provide information as to deformation and shape of the membrane.

Figure 1:
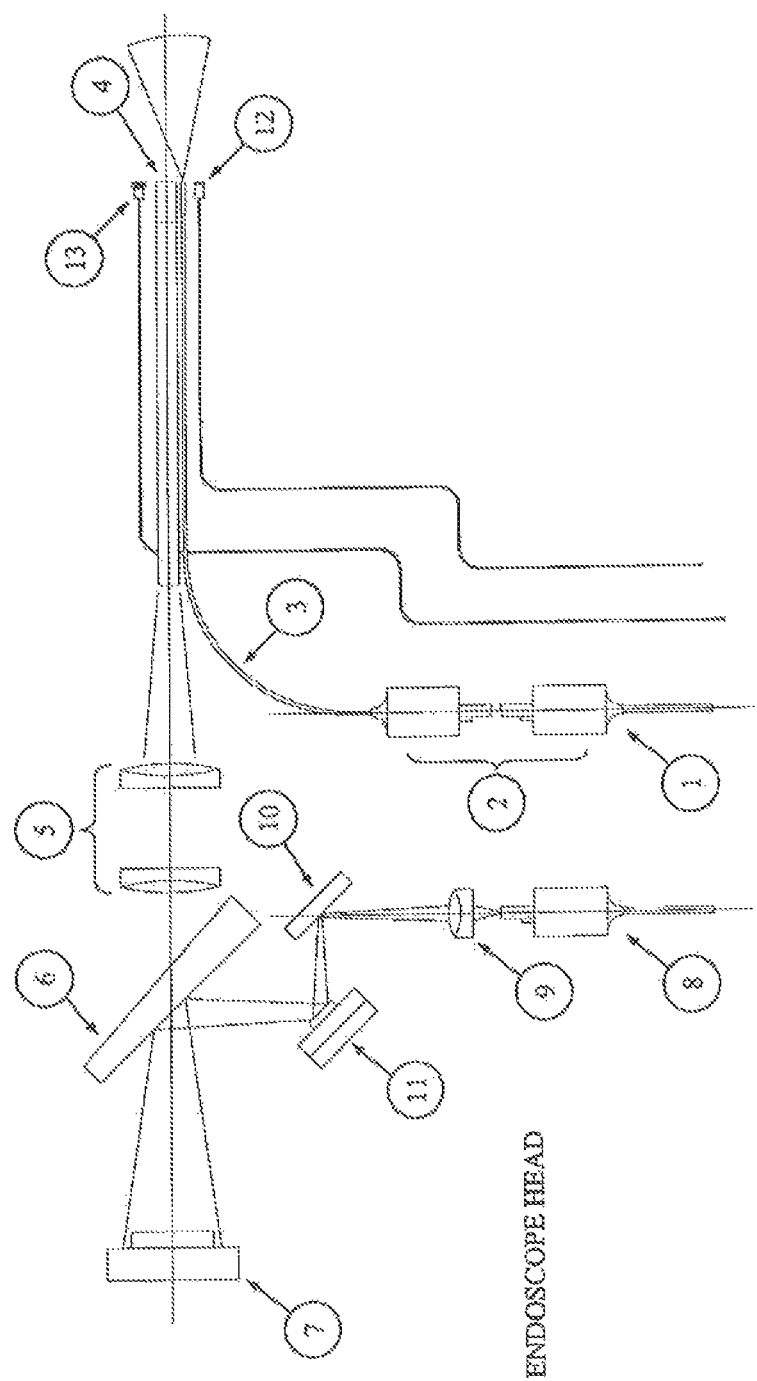
FIG. 1 is a graphical schematic representation of an embodiment of the system of these teachings.
Figure 2:
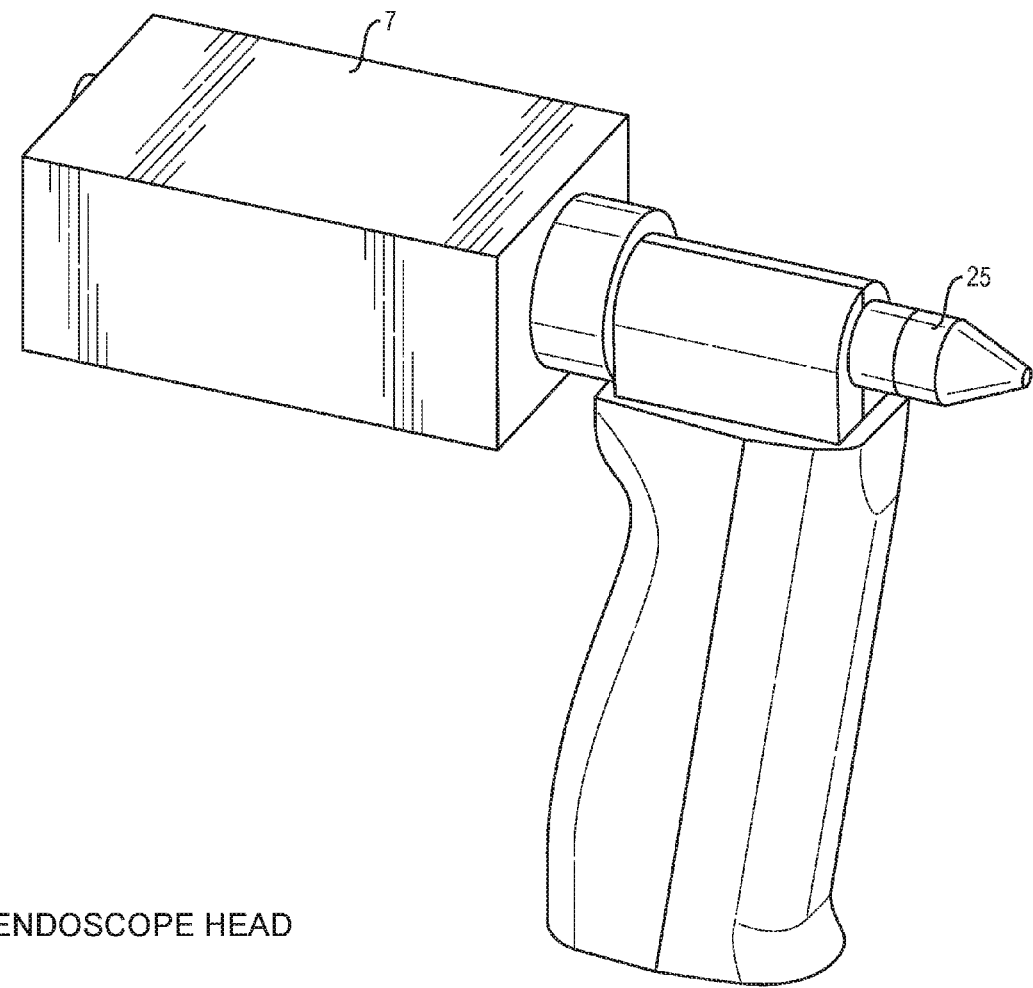
FIG. 2 is a graphical representation of an embodiment of the system of these teachings.
Figure 3:
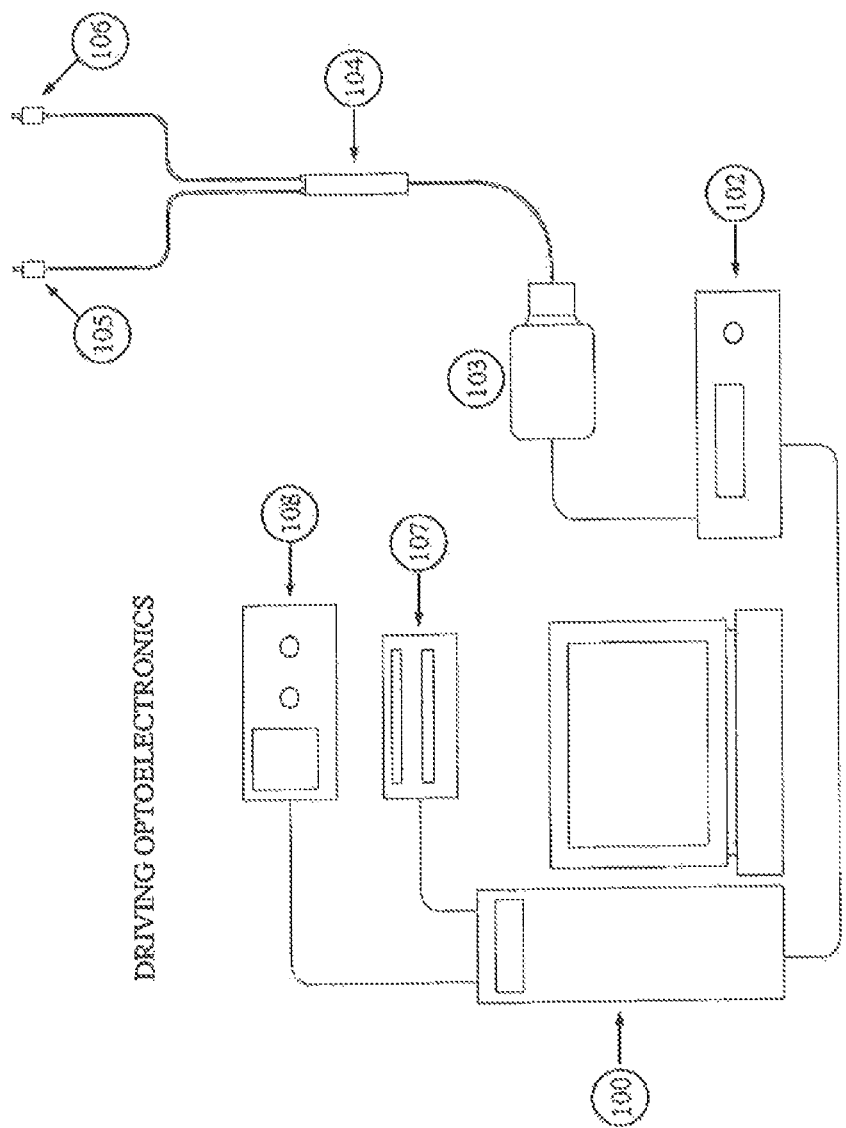
FIG. 3 is a graphical schematic presentation of a component of an embodiment of the system of these teachings.

FIGS. 1-3 show different aspects of an embodiment of the system of this invention. Referring to FIG. 1, a HEMS based microphone 12 (an embodiment of a sound receiving component) and a MEMS-based sound generator 13 (an embodiment of a sound generating component) are disposed on the periphery of a GRIN lens assembly 4 (an embodiment of an optical component). (Exemplary embodiments of MEMS based microphones include, but are not limited to, the embodiments described in "MEMS Microphone Enables Better Acoustic Designs," ECN 7/1/206 available at http://www.ecnmag.com/article/CA623592.html, incorporated by reference herein. Exemplary embodiments of MEMS-based sound generators include, but not limited to, the embodiments described in US Patent Application Publication number 20060153418, incorporated by reference herein.) A source of electromagnetic radiation provides a fiber-optic object illumination beam 1 coupled by a fiber to fiber connector 2 to a fiber-optic component 3 terminating on a lens at the end opposite to the end connected to the fiber-to-fiber connector 2 (the structure being an embodiment of a light delivery component). (In one embodiment, the lens could be attached. In another embodiment, the lens could be integrated into the fiber. Other embodiments are also within the scope of these teachings.) The end of the fiber component 3 that has the lens attached is also disposed on the periphery of the GRIN lens assembly 4. As shown in FIG. 2, the GRIN lens assembly 4, the end of the fiber component 3 that has the lens attached, the MEMS based microphone 12 and the MMES-based sound generator 13 are all adapted to be located in a speculum 25, the speculum 25 being adapted to permit examination of a passage (such as an ear passage). The end of the fiber component 3 that has the lens attached is capable of delivering light into the passage. The GRIN lens assembly 4 is capable of receiving a reflected/scattered portion of the light delivered into the passage. An imaging component (imaging lenses in the embodiment shown, although other embodiments are within the scope of these teachings) 5 is optically disposed to receive the reflected/scattered portion of the light that is transmitted by the GRIN lens assembly 4. A reference beam source fiber optic component 8 provides a reference light beam that is imaged by a collimating lens assembly 9 onto a beam steering mirror 10. The reference light beam is reflected by the beam steering mirror 10 onto a MEMS micromirror 11 (an embodiment of our modulating component) that is capable of temporally (in the embodiment shown) modulating the reference light beam. The MEMS micromirror 11 reflects the temporarily modulated reference light beam on to the back facet of the beam splitter wedge 6 (the beam splitter wedge being an embodiment of the other optical component, other embodiments being within the scope of these teachings). The reflected/scattered portion of the light transmitted through the imaging component 5 is incident on the front facet of the beam splitter wedge 6 and is transmitted through the beam splitter wedge 6. Both the reflected/scattered portion of the light and the reflected temporally modulated reference light beam are incident on an image detecting component (a digital camera in the embodiment shown, other embodiments being within the scope of this teachings) 7. The digital camera 7 detects an interferometric recording (holographic recording) of the temporally modulated reference light beam and the reflected/scattered portion of the light delivered into the passage. The holographic recording can provide information as to deformation and shape of a membrane in the passage. The MEMS-based sound generator 13 can excite the membrane in order to observe membrane characteristics or behaviors. The MEMS-based microphone 12 can record in the acoustic signal generated by the MEMS-based sound generator 13 and provide information regarding the sound pressure levels.

FIG. 2 shows a graphical representation of an embodiment of the system of these teachings. FIG. 3 shows the electronic and optical components of an embodiment of the system of these teachings. The components shown in FIG. 3 include a computer subsystem 100 (such as a personal computer), used for data collection, holographic image processing, signal generation and control (including subsystem driving signals), and is capable of providing signals to a frequency generator 108 that drives the MEMS-based sound generator 13 and a laser diode controller 102 and of receiving signals from an input terminal 107 for the MEMS-based microphone 12. The laser diode controller 102 drives a laser diode 103 that is fiber coupled to a fiber-optic directional coupler 104. The fiber-optic directional coupler 104 splits the beam from the laser diode 103 into a fiber-optic coupled reference beam 105 and a fiber-optic coupled object illumination beam 106. The computer subsystem 100 receives the holographic recording from the digital camera 7 and is capable of processing the holographic recording in order to obtain deformation data and shape measurements for the membrane.

An exemplary embodiment of the methods for obtaining deformation data and shape measurements for the membrane is given below. It should be noted that these teachings are not limited only to this exemplary embodiment. Images acquired by the digital camera 7 are processed by the computer 100 to provide quantitative measurements of deformations and shape of the samples of interest. Processing, in the embodiment described below, is based on spatial intensity distributions, $I_n(u,v)$, defined at the imaging plane $(u,v)$, and recorded by the camera, i.e., $$I_n(u,v) = I_o(u,v) + I_r(u,v) + \sqrt{I_o(u,v)I_r(u,v)} \cos [\Delta\phi(u,v) + \theta_n + \Omega(u,v)], \quad (1)$$

where $I_o(u,v)$ and $I_r(u,v)$ represent intensities of the two interfering beams (the reflected object and reference beams), $\Delta\phi(u,v)$ represents the optical phase difference between the two beams, and $\theta_n$ is the phase associated with the n-th light path length, produced by the MEMS micromirror 11, that is imposed during recording of the n-th image to facilitate determination of the fringe-locus function $\Omega(u,v)$. The fringe locus is related to displacements and deformations of the samples of interest. If, for example, this teachings not being limited to only this example, n=5, (e.g. 0, 0.25, 0.5, 0.75 and 1 period of light wavelength) $\Omega(u,v)$ is determined from 5 intensity distributions, described by Eq. 1, yielding $$\Omega(u, v) = \tan^{-1}\left\{ \frac{2[I_4(u, v) - I_2(u, v)]}{-I_1(u, v) + 2I_3(u, v) - I_5(u, v)} \right\}. \quad (2)$$

Because of the nature of the inverse tangent function in Eq. 2, the fringe-locus function, $\Omega(u,v)$, is obtained wrapped modulo $2\pi$. Recovery of continuous spatial phase distributions requires the application of efficient phase unwrapping algorithms. (A review of phase unwrapping algorithms is provided in Kaplan, Ulrich, Phase Unwrapping: A Review of Methods and a Novel Technique, presented at the 2007 CSPG CSEG convention, which is incorporated by reference herein in its entirety; see also, Zimmnermann, K. P., "On frequency-domain and time-domain phase unwrapping," *Proceedings of the IEEE*, vol. 75, no. 4, pp. 519-520, April 1987, and Tribolet, J., "A new phase unwrapping algorithm," *IEEE Transactions on Acoustics, Speech, and Signal Processing*, vol. 25, no. 2, pp. 170-177, April 1977, both of which are also incorporated by reference in their entirety; see also C. Furlong and R. J. Pryputniewicz, "Absolute shape measurements using high-resolution optoelectronic holography methods," invited paper, special issue on optical shape measurement techniques, *J. Opt. Eng.*, 39(1):216-223, 2000, which is also incorporated by reference in its entirety.) The fringe-locus function determined after phase unwrapping Eq. 2 and transformed to the absolute coordinate system (x,y)

$$\Omega(u,v) \Rightarrow \Omega(x,y), \quad (3)$$

relates to measurements of the vector L(x,y) by equations (1-3)

$$K(x,y) \cdot L(x,y) = \Omega(x,y), \quad (4)$$

where $K=K_2-K_1$ is the sensitivity vector characterizing the geometry of the miniaturized optical setup defined by the vectors of illumination and observation directions, $K_1$ and $K_2$, respectively. L(x,y) computed from Eq. 4 provides direct quantitative measurements of deformations and shape of samples of interest. (Exemplary determination of L(x,y) from Eq. 4 is given in R. J. Pryputniewicz, 1995, "Quantitative determination of displacements and strains from holograms," Ch. 3 in *Holographic interferometry*, Vol. 68 of Springer Series in Sciences, Springer-Verlag, Berlin, Germany, pp. 33-72, which is incorporated by reference herein in its entirety, and in Ryszard J. Pryputniewicz "Pulsed laser holography in studies of bone motions and deformations," J. Opt. Eng., Vol. 24, No. 5, 1985, pp. 832-839, which is also incorporated by reference herein in its entirety.)

In stroboscopic mode, quantitative measurements are obtained by measuring $\Omega_n(x,y)$, corresponding to varied states of deformation (e.g. over 8 phases of a tonal stimulus period). The difference, $$\Delta\Omega(x,y) = \Omega_j(x,y) - \Omega_i(x,y), \quad (5)$$

provides a direct measurement of the deformations between two states of interest. In an embodiment of the system of these teachings, the difference $\Delta\Omega(x,y)$ is evaluated and displayed at video-rates via specialized image processing hardware and software.

In time-averaged mode, quantitative measurements are obtained by performing continuous acquisition and exposure of the camera to provide intensity distributions of the form $$I(x, y) = \frac{1}{\Delta t} \int_{t}^{t+\Delta t} I_t(x, y, t) dt, \quad (6)$$

in which $\Delta t$ is the exposure time of the camera. By varying the length of the reference light path by n fractions of a wavelength, the n-th intensity distribution in time-average mode is $$I_n(x,y) = I_o(x,y) + I_r(x,y) + \sqrt{I_o(x,y)I_r(x,y)} \cos [\Delta\phi(x,y) + \theta_n] \cdot M[\Omega_t(x,y)], \quad (7)$$

where $M[\Omega_t(x,y)]$ is the characteristic function determined by the temporal motion of the sample under investigation. For the case of a sample excited by sinusoidal functions with period much shorter than the exposure time of the camera, $$M[\Omega_t(x,y)] = J_o[\Omega_t(x,y)], \quad (8)$$

where $J_o(x,y)$ is the zero-order Bessel function of the first kind. In the time-averaged mode, interference patterns of the form $$I_d(x,y) = 4\sqrt{I_o(x,y)I_r(x,y)} |M[\Omega_t(x,y)]|, \quad (9)$$

are also evaluated and displayed at video-rates to enable the capability of fast identification and evaluation of mode shapes and resonant frequencies of samples of interest (31,111-3,117).

Shape measurements are performed in the stroboscopic mode by acquiring sets of images using optical wavelength $\lambda_1$ (representing a reference state), and then acquiring a set of images after optical wavelength has been changed or tuned to $\lambda_2$. The phase change related to shape contours $\gamma$ (x,y) obtained after performing this double-exposure operation is equivalent to the fringe-locus function $\Omega(x,y)$, as in the static mode. Changing or tuning of the optical wavelength is equivalent to static measurements with a synthetic optical wavelength, $\Lambda$, which is determined by $$\Lambda = \frac{\lambda_1 \lambda_2}{|\lambda_2 - \lambda_1|} \quad (10)$$

Changing or tuning of the optical wavelength can be performed using a tunable light source (in one exemplary embodiment, these teachings not being limited to only that embodiment, an infrared master-oscillator-power-amplifier (MOPA) laser diode, capable of wavelength tuning by thermoelectric diode stage cooling).

In using the embodiment shown in FIGS. 1-3, an excitation of the MEMS-based sound generator 13 is selected by the computer 100 and provided by the frequency generator 108 to the MEMS-based sound generator 13. The sound generated by the MEMS-based sound generator 13 enters the passage and excites the membrane in the passage. The MEMS-based sound microphone 12 samples the sound pressure levels in the passage, which are caused by the generated sound and the vibration of the membrane. An illuminating beam provides light into the passage and the illuminating beam light is reflected/scattered by the vibrating membrane. The reflected/scattered light is received by the GRIN lens assembly 4 and imaged onto the optical imaging component 5. The optical imaging component 5 images the received reflected/scattered light through the beam splitter wedge 6 onto the digital camera 7. The fiber-optic reference beam 8 is imaged onto the temporal modulation component 11 utilized for modulating the reference beam 8. The modulated reference beam is reflected by the beam splitter wedge 6 and imaged onto the digital camera 7, thereby creating an interference pattern with the reflected/scattered light and producing an interferometric recording (holographic recording), recorded on the digital camera 7. The interferometric recording data is provided to the computer 100 where it is analyzed. Deformation data and shape measurements for the membrane are obtained from analyzing the interferometric recording data. Based on previously determined information, when the passage and the membrane are the middle ear and the tympanic membrane, information regarding ossicular disorders and evaluation of middle ear reconstruction can be obtained.

The above described application of the embodiment of the system of these teachings shown in FIGS. 1-3 details one embodiment of the method of these teachings. The embodiment disclosed hereinabove, when the passage and the membrane are the middle ear and the tympanic membrane (also referred to herein as the inner ear), can be further described as including exciting the inner ear with a predetermined acoustic input, detecting a response to inner ear excitation by the predetermined acoustic input, providing an incident light into inner ear, while the inner ear is responding to the inner ear excitation, receiving a portion of the incident light, the portion being reflected/scattered due to the inner ear excitation, obtaining an interference pattern from the received portion of the incident light and a reference lightbeam and analyzing the interference pattern to determine spatial/temporal information related to inner ear function. In one instance the embodiment of the method of these teachings includes controllably deflecting the reference lightbeam.

In another instance, the step of obtaining an interference pattern also includes (a) varying, by the controllable deflection, a length of a path of the reference lightbeam by a predetermined fraction of a wavelength; (b) obtaining an intensity distribution corresponding to an interference pattern between the received portion of the incident light and the reference lightbeam after traversing the length of the path; and (c) repeating steps a) and b) for a number of predetermined fractions of the wavelength; thereby obtaining a number of intensity distributions, and the step of analyzing the interference pattern includes obtaining a predetermined function of the intensity distributions, the predetermined function being related to characteristics of the excitation of the inner ear, and obtaining from the predetermined function characteristics of the excitation of the inner ear. In one instance, the intensity distributions are given by $$I_n(u,v)=I_o(u,v)+I_r(u,v)+\sqrt{I_o(u,v)I_r(u,v)} \cos [\Delta\phi(u,v)+ \theta_n+\Omega(u,v)], n=1 \text{ to } N, \quad (11)$$

and the predetermined function is the fringe-locus function, $\Omega(u,v)$. For the exemplary embodiment where N=5, (e.g. 0, 0.25, 0.5, 0.75 and 1 period of light wavelength) $\Omega(u,v)$ is determined from 5 intensity distributions, yielding $$\Omega(u, v) = \tan^{-1}\left\{\frac{2[I_4(u, v) - I_2(u, v)]}{-I_1(u, v) + 2I_3(u, v) - I_5(u, v)}\right\} \quad (12)$$

The function is related to characteristics of the excitation of the inner ear by the relation to measurements of the vector L(x,y) through $$K(x,y)\cdot L(x,y)=\Omega(x,y) \quad (13)$$

where $K=K_2-K_1$ is the sensitivity vector characterizing the geometry of the miniaturized optical setup defined by the vectors of illumination and observation directions, $K_1$ and $K_2$, respectively. By inverting the above equation, L(x,y) is obtained (see, for example, but not limited to, R. J. Pryputniewicz, 1995, "Quantitative determination of displacements and strains from holograms," Ch. 3 in *Holographic interfermetry*, Vol. 68 of Springer Series in Sciences, Springer-Verlag, Berlin, Germany, pp. 33-72, which is incorporated by reference herein in its entirety). The embodiment can also include applying a phase unwrapping algorithm to the predetermined function. In another instance, each intensity distribution is obtained over a predetermined time period.

In another instance, obtaining an interference pattern also includes repeating step a), b), and c) herein above at a number of time periods, the time periods being selected over a characteristic time period of the response to excitation, and the step of analyzing the interference pattern also includes obtaining a number of predetermined functions, each predetermined function from being obtained at a different time period from the plurality of time period, obtaining a difference between one predetermined function and another predetermined function, the one predetermined function and the other predetermined function being obtained at consecutive time periods, and obtaining, from the difference, characteristics of a temporal evolution of the excitation of the inner ear.

In embodiments in which a wavelength of the illuminating light source and the reference light source is selectable to a predetermined wavelength, obtaining an interference pattern includes provide control signals to the modulating components, the control signals resulting in varying a length of a path of light from the reference light source by a predetermined phase increment; an intensity distribution being obtained corresponding to the interferometric recording between the reflected scattered portion of the light delivered into the passage at the first wavelength and the light from the reference light source at the first wavelength after traversing the length of the path, and repeating the preceding instruction for a number of predetermined phase increments; thereby obtaining a first group of intensity distributions, selecting the wavelength of the illuminating light source and the reference light source to a second wavelength, providing control signals to the modulating components, the control signals resulting in varying a length of a path of light from the reference light source by a predetermined phase increment, an intensity distribution being obtained corresponding to the interferometric recording between the reflected scattered portion of the light delivered into the passage at the second wavelength and the light from the reference light source at the second wavelength after traversing the length of the path, and repeating the preceding instruction for a number of predetermined phase increments; thereby obtaining a second plurality of intensity distributions, obtaining, from the first and second groups of intensity distributions, a predetermined function; the predetermined function related to spatial characteristics of a response of the membrane to excitation, obtaining, from the predetermined function, spatial characteristics of the response of the membrane to excitation.

In an exemplary embodiment, the first group of intensity distributions is given by $$=I_E(u,v)+I_M(u,v)\cos\left[\Delta\phi(u,v)+\theta_n\right], \quad (14)$$

where n=1, 2 . . . 4, and the second group of intensity distributions is given by $$I'_n(u,v)=I_g(u,v)+I_M(u,v)\times\cos\left[\Delta\phi(u,v)+\Delta\gamma(u,v)+\theta'_n\right], \quad (15)$$

where $\Delta\gamma(u,v)$ is the spatial optical phase difference resulting from the change in the wave numbers and related to the absolute shape of the object under investigation, and $\theta'_n$ is the imposed n'th known phase step. $\Delta\gamma(u,v)$, for the case where an equals four, can be evaluated as $$-\arctan\left[-\frac{(I_1-I_3)(I'_2-I'_4)-(I_2-I_4)(I'_1-I'_3)}{(I_1-I_3)(I'_2-I'_4)+(I_2-I_4)(I'_1-I'_3)}\right], \quad (16)$$

and can be related to the actual physical shape by noting that $$\Delta\gamma=2\pi(\text{Optical path length})/\Lambda, \quad (17)$$

where $\Lambda$ is defined in equation and 10 herein above. The optical path length is defined as the distance from the point of illumination to a point in the shape of interest and to the point of observation. The above equation can be solved for the shape of interest (see, for example, C. Furlong and R. J. Pryputniewicz, "Absolute shape measurements using high-resolution opto-electronic holography methods," invited paper, special issue on optical shape measurement techniques, J. Opt. Eng., 39(1):216-223, 2000, which is also incorporated by reference in its entirety).

Although the above description of the method of these teachings was based on the embodiment shown in FIGS. 1-3, the method is not limited only to that embodiment.

Figure 4:
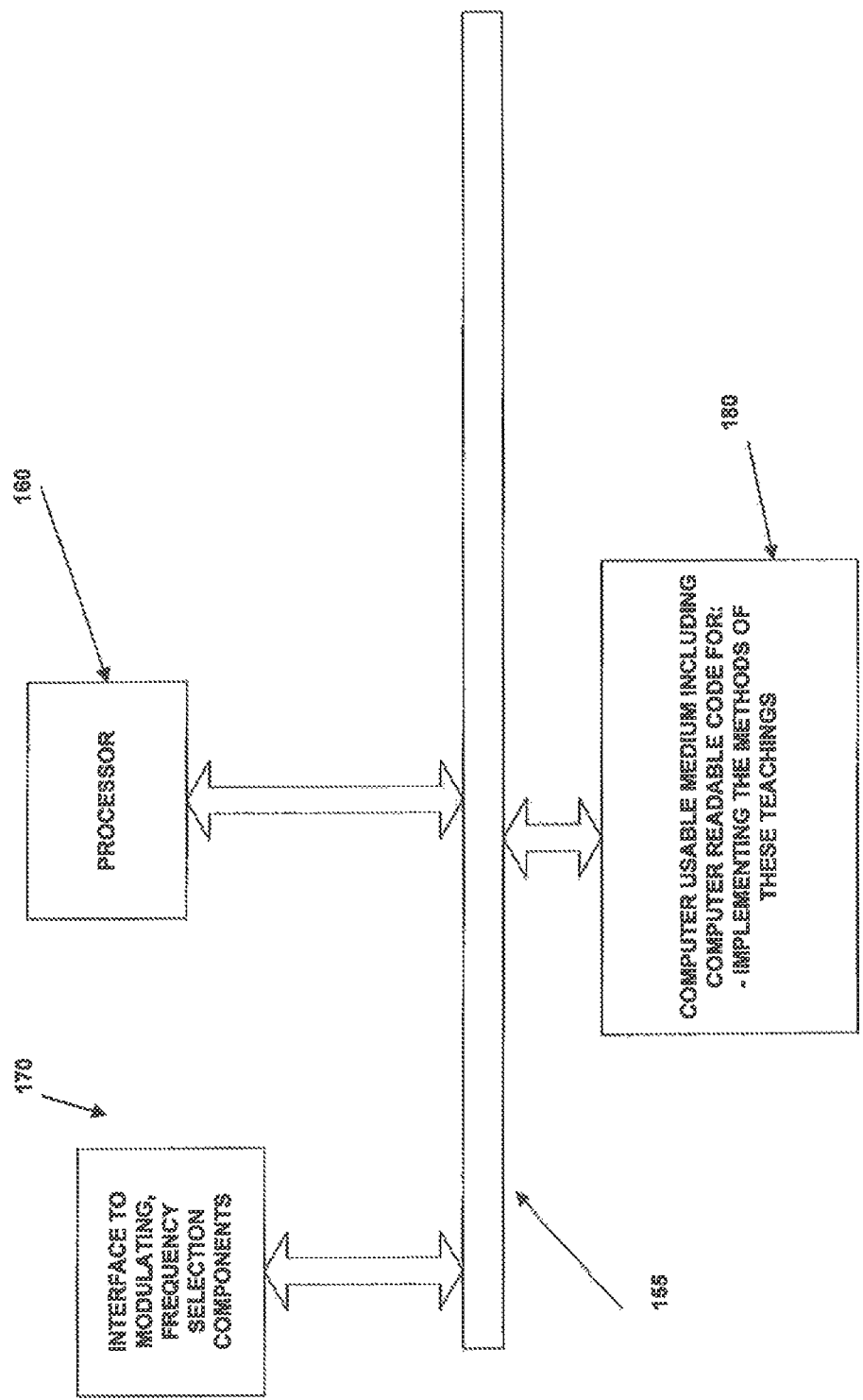
FIG. 4 is a graphical schematic presentation of another component of an embodiment of the system of these teachings.

In one embodiment, shown in FIG. 4, the computer 100 includes one or more processors 160 and one or more computer usable media 180 having computer readable code embodied therein to cause the one or more processors 160 to implement the methods of these teachings. Also shown in FIG. 4 is an interface 170 from the computer 100 to the controls for the modulating component and for the frequency modifying component. The one or more processors 160, the one or more computer usable media 180 and the interface 170 are operatively connected by connection means 155 (such as, but not limited to, a computer bus). The one or more computer usable media 180 can cause the one or more processors 160 to send control signals to the modulating component 11 or to select the frequency of a tunable light source by providing other control signals.

In general, the techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to data entered using the input device to perform the functions described and to generate output information. The output information may be applied to one or more output devices.

Elements and components described herein may be further divided into additional components or joined together to form fewer components for performing the same functions. Each computer program within the scope of the claims below may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable media include, for example, a floppy disk, a flexible disk, hard disk, magnetic tape, or any other magnetic medium, a CDROM, any other optical medium, punched cards, paper tape, any other physical medium with patterns of holes, a RAM, a PROM, and EPROM, a FLASH-EPROM, any other memory chip or cartridge, or any other medium from which a computer can read. From a technological standpoint, a signal or carrier wave (such as used for Internet distribution of software) encoded with functional descriptive material is similar to a computer-readable medium encoded with functional descriptive material, in that they both create a functional interrelationship with a computer. In other words, a computer is able to execute the encoded functions, regardless of whether the format is a disk or a signal.

Although the teachings have been described with respect to various embodiments, it should be realized these teachings are also capable of a wide variety of further and other embodiments within the spirit and scope of the appended claims.

The invention claimed is:

1. A system for observation of two dimensional deformation and two dimensional shape of an inner ear membrane, the system comprising:
   a transducer that emits a predetermined acoustic input to excite an inner ear;
   a microphone to detect a response to inner excitation by the predetermined acoustic input;
   a speculum configured to examine the inner ear, the speculum comprising:
      a laser diode operatively connected to an optical fiber to provide an incident light into the inner ear while the inner ear is responding to the predetermined acoustic input;
      a gradient-index (GRIN) lens to receive a portion of the incident light, said portion being reflected or scattered due to the light inner ear excitation; and
      an imaging lens disposed to receive the portion of the incident light from said GRIN lens;

a reference optical fiber light source that emits a reference light beam and a micromirror disposed to receive the reference light beam and configured to modulate the reference light beam;

a beam splitter wedge disposed to receive the modulated light from said micromirror and the portion of the incident light from said imaging lens, said beam splitter wedge further providing light to a digital camera; wherein the digital camera obtains an interferometric recording from the received portion of the incident light, the reference lightbeam and the light received from the beam splitter wedge;

a computer having computer code instructions stored thereon, the computer code instructions being configured to cause the computer to:

analyze the interferometric recording to determine spatial and temporal information related to inner ear function; the spatial and temporal information comprising the two dimensional deformation and two dimensional shape of the inner ear membrane;

wherein obtaining the interferometric recording further comprises providing control signals to said micromirror to:

a) vary, by controllable deflection, a length of a path of the reference lightbeam by a predetermined fraction of a wavelength;

b) obtain an intensity distribution corresponding to the interferometric recording between the reflected or scattered portion of the incident light and the reference lightbeam after traversing said length of said path; and c) repeat steps a) and b) for a number of predetermined fractions of the wavelength; thereby obtaining a plurality of intensity distributions in order to obtain a predetermined function characteristic of the inner ear which correlates with spatial and temporal information.

2. The system of claim 1 wherein said computer code instructions, in causing said computer to analyze the interferometric recording, further causes said computer to:
apply a phase unwrapping algorithm to said predetermined function.

3. The system of claim 1 wherein said computer code instructions, in causing said computer to analyze the interferometric recording, causes said computer to:

a) provide control signals to said micromirror, said control signals resulting in varying a length of a path of light from said reference optical fiber light source by a predetermined fraction of a wavelength; an intensity distribution being obtained corresponding to the interferometric recording between the reflected or scattered portion of the light delivered into an ear passage and the light from said reference optical fiber light source after traversing said length of said path; and b) repeat instruction a) for the number of predetermined fractions of the wavelength; thereby obtaining the plurality of intensity distributions;

c) repeat steps a) and b) at a plurality of time periods, said plurality of time periods being selected over a characteristic time period of a response of the inner ear membrane to excitation;

obtain a plurality of predetermined functions, each predetermined function from said plurality of predetermined functions being obtained at a different time period from said plurality of time periods from said plurality of intensity distributions at said different time period;

obtain a difference between one predetermined function from said plurality of predetermined functions and another predetermined function from said plurality of predetermined functions; said one predetermined function and said another predetermined function being obtained at consecutive time periods from said plurality of time periods; and obtain, from said difference, characteristics of a temporal response of the inner ear membrane to excitation.

4. The system of claim 3 wherein said computer code instructions, in causing said computer to analyze the interferometric recording, further causes said computer to:
apply a phase unwrapping algorithm to each predetermined function from said plurality of predetermined functions.

5. The system of claim 1 wherein a wavelength of said laser diode and said reference optical fiber light source is selectable to a predetermined wavelength; and wherein said computer code instructions, in causing said computer to analyze the interferometric recording, causes said computer to:

select the wavelength of said laser diode and said reference optical fiber light source to a first wavelength;

provide control signals to said micromirror, said control signals resulting in varying a length of a path of light from said reference optical fiber light source by a predetermined phase increment; an intensity distribution being obtained corresponding to the interferometric recording between the reflected or scattered portion of the light delivered into the ear passage at said first wavelength and the light from said reference optical fiber light source at said first wavelength after traversing said length of said path; and repeat the preceding instruction for a number of predetermined phase increments; thereby obtaining a first plurality of intensity distributions;

select the wavelength of said laser diode and said reference optical fiber light source to a second wavelength;

provide control signals to said micromirror, said control signals resulting in varying a length of a path of light from said reference optical fiber light source by a predetermined phase increment; an intensity distribution being obtained corresponding to the interferometric recording between the reflected or scattered portion of the light delivered into the ear passage at said second wavelength and the light from said reference optical fiber light source at said second wavelength after traversing said length of said path;

repeat the preceding instruction for a number of predetermined phase increments; thereby obtaining a second plurality of intensity distributions;

obtain, from said first and second pluralities of intensity distributions, a predetermined function; said predetermined function related to spatial characteristics of a response of an inner ear membrane to excitation; and obtain, from said predetermined function, spatial characteristics of the response of the inner ear membrane to excitation.

6. The system of claim 1 wherein each intensity distribution from said plurality of intensity distributions is obtained over a predetermined time period.

* * * * *